(12) United States Patent  
Lavitrano et al.

(10) Patent No.: US 9,068,200 B2  
(45) Date of Patent: Jun. 30, 2015

(54) METHOD FOR THE TRANSFER OF EPISOMAL VECTORS INTO ANIMAL CELLS

(75) Inventors: Marialuisa Lavitrano, Milan (IT); Maria Laura Bacci, Bologna (IT); Monica Forni, Bologna (IT); Hans Joachim Lipps, Tubingen (DE); Pierluigi Donini, Rome (IT)

(73) Assignee: UNIVERSITA' DEGLI STUDI MILANO-BICOCCA, Milan (IT)

( * ) Notice: Subject to any disclaimer, the term of this patent is extended or adjusted under 35 U.S.C. 154(b) by 1320 days.

(21) Appl. No.: 12/089,047

(22) PCT Filed: Oct. 5, 2005

(86) PCT No.: PCT/IT2005/000573  
§ 371 (c)(1),  
(2), (4) Date: Aug. 28, 2008

(87) PCT Pub. No.: WO2007/039920  
PCT Pub. Date: Apr. 12, 2007

(65) Prior Publication Data  
US 2009/0158450 A1    Jun. 18, 2009

(51) Int. Cl.  
*C12N 15/00*    (2006.01)  
*C12N 15/877*   (2010.01)

(52) U.S. Cl.  
CPC ....... *C12N 15/8778* (2013.01); *A01K 2227/108* (2013.01); *C12N 2517/10* (2013.01); *C12N 2800/108* (2013.01); *C12N 2830/46* (2013.01)

(58) Field of Classification Search  
None  
See application file for complete search history.

(56) References Cited

U.S. PATENT DOCUMENTS 6,410,314 B1 * 6/2002 Baiker et al. ............... 435/320.1  
2002/0086428 A1   7/2002 Jelesko et al.

FOREIGN PATENT DOCUMENTS

WO    02/34040    5/2002  
WO    02/43478    6/2002  
WO    02/068669   9/2002

OTHER PUBLICATIONS

Anzar et al. Theriogenol 2006;65:683-90, published online Jul. 2005.*  
PCT Search Report for PCT/IT2005/000573 filed on Oct. 5, 2005 in the name of Universita' degli Studi Di Milano—Bicocca.  
PCT Written Opinion for PCT/IT2005/000573 filed on Oct. 5, 2005 in the name of Universita' degli Studi Di Milano—Bicocca.  
Bode et al., "Biological Significance of Unwinding Capability of Nuclear Matrix-Associating DNAs", Jan. 1992, Science 255, 195-197.  
Ebersole et al., Mammalian artificial chromosome formation from circular alphoid input DNA does not require telomere repeats, Hum. Mol. Genet 9, 1623-1631, 2000.  
Fantinati et al., "Laparoscopic insemination technique with low numbers of spermatozoa in superovulated prepuberal gifts for biotechnological application", Theriogenology 63, 2005, pp. 806-817.  
Farr et al., Generation of human X-derived mini Chromosome using telomere-associated 25 chromosome fragmentation, EMBO J. 14, 54444-5454 , 1995.  
Glover et al., "Towards Safe, Non-Viral Therapeutic Gene Expression in Humans" Nature Reviews Genetics, vol. 61 Apr. 2005, pp. 299-311.  
Goetze. S., Gluah, A., Benham, C., Bode, J. "Computational and in vitro analysis of destabilized DNA regions in the interferon cluster. Potential of predicting functional domains", Biochemistry 42, 154-166, 2003.  
Heller et al., "Minichromasomes derived from the human Y chromosome by telomere directed chromosome breakages", Proc. Natl. Acad. Sci, USA 93, 7125-7130, 1996.  
Hirt, B., "Selective Extraction of Polyoma DNA from Infected Mouse Cell Cultures", J. *Mol. Biol.* (1967) 26, 365-369.  
Jenke at al., "Nuclear scaffold/matrix attached region modules liked to a transcription unit are, sufficient for replication and maintenance of a mammalian episome", Methods, PNAS, Aug. 3, 2004, vol. 101, No. 31.  
Krawetz, B.A., Draghici, S., Goodrich, R.; Liu, Z. Ostermeier,. G.C., "In silico and wet-bench identification of nuclear matrix attached regions", Meth. Mol. Med. 2004, 439-458.  
Lavitrano, M. et al., "Efficient production by sperm-mediated gene transfer of human decay accelerating factor (hDAF) transgenic pigs for xenotransplantation", PNAS, Oct. 29, 2002, vol. 99 , No. 22, pp. 14230-14235.  
Lavitrano, M. et al., "Sperm Cells as Vectors for Introducing Foreign DNA into Eggs: Genetic Transformation of Mice", 1989, Cell, vol. 57 No. 5, pp. 717-723.  
Lavitrano, M. et al., "Sperm Mediated Gene Transfer in pig: Selection of donor boars and optimization of DNA uptake." Evaluation of Semen Quality, Molecular Reproduction and Development 64:284-291, 2003.  
Luderus, M. E. et al., "Binding of Matrix Attachment Regions to Lamin Polymers Involves Single-Stranded Regions and the Minor Groove", Molecular & Cellular Biology, 1994, vol. 14, pp. 6297,-6305.  
Piechaczek et al., "A vector based on the SV40 origin of replication and chromosomal S/MARs replicates episomally in CHO cells" Nucleic Acids Research 1999, vol. 27, No. 2, 426-428.

(Continued)

*Primary Examiner* — Janice Li  
(74) *Attorney, Agent, or Firm* — Steinfl & Bruno LLP (57) ABSTRACT

The present invention refers to a method for the transfer of DNA sequences or exogenous genes into animal sperm cells by means of the use of episomal vectors. The invention also relates to the use of "Sperm Mediated Gene Transfer" (SMGT) technology for the creation of genetically modified individuals.

34 Claims, 10 Drawing Sheets

(56) References Cited

OTHER PUBLICATIONS

Elbrecht A et al: "Episomal Maintenance of Abovine Papilloma Virus Vector in Transgenic Mice" Molecular and Cellular Biology, Washington, DC, US, vol. 7, No. 3, Mar. 1, 1987, pp. 1276-1279.

Carballada R et al: "Regulation of foreign DNA uptake by mouse spermatozoa" Experimental Cell Research, San Diego, CA, US, vol. 262, No. 2, Jan. 15, 2001, pp. 104-113.

Maione B et al: "Sperm-Mediated Gene Transfer in Mice" Molecular Reproduction and Development, Lisss, New York, NY, US, vol. 50, Aug. 1998, pp. 406-409.

Ingermann, RL, et al., Carbon dioxide and pH affect sperm mobility of white sturgeon (*Acipenser transmontanus*), The Journal of Experimental Biology 2002, 205: 2885-2890.

\* cited by examiner

METHOD FOR THE TRANSFER OF EPISOMAL VECTORS INTO ANIMAL CELLS

CROSS REFERENCE TO RELATED APPLICATIONS

This application is the national phase of International Application PCT/T2005/000573 filed on Oct. 5, 2005.

FIELD OF THE INVENTION

The present invention relates to a method for the transfer of DNA sequences and/or exogenous genes into animal cells, and in particular, to a method for the transfer of nucleotide sequences into sperm cells. Furthermore, the invention relates to the use of sperm cells, thus modified, for the fertilisation of egg cells so as to create transgenic animals or genetically modified individuals.

BACKGROUND OF THE ART

The creation of transgenic animals or genetically modified individuals, i.e. individuals whose genome has been modified by the permanent introduction of exogenous DNA, has assumed ever greater importance for example in gene regulation studies, for therapeutic goals and for livestock production. In particular, certain animals may be created in order to increase milk production, to be resistant to pathogens, for experimental use in the development of novel drugs or, even, for xenotransplantation.

However, to date, the creation of such animals is very complex and problematic.

Xenotransplantation, for example, belongs to a particular branch of biotechnology and medicine involved in the transplantation of cells, tissues and organs derived from individuals belonging to different species. This branch has been known for some time but encounters significant difficulties in practical application, due to problems associated with the rejection of the transplanted organs. Indeed, it is known that the immune system of the recipient body recognises the transplanted organ as extraneous, and initiates a series of reactions leading to the so-called rejection of the extraneous organ.

The aim of clinical xenotransplantation could be that of substituting a diseased human organ with organs from animals, under such conditions whereby the problem of rejection is avoided.

In order to settle this problem, along with the problems associated with the production of animals for other purposes such as those listed above, the creation of transgenic animals, or rather animals which have been genetically modified so as to carry defined genetic sequences normally not present in their genomes, has been proposed. In other words, there is an attempt to insert DNA sequences, encoding the expression of proteins which help avoid the above mentioned problems relating to rejection, into the DNA of certain target animals.

Generally, the technique most commonly used for the insertion of exogenous DNA into animal cells consists in the microinjection of exogenous DNA into the male pronucleus of a zygote. This technique, even though it has proved to be successful in mice, has not shown any degree of success in livestock, such as pigs, which are of significant interest for xenotransplantation and other biotechnologies, thereby limiting its general use.

Lavitrano et al. (1989, Cell 57, 717-723) have proposed an alternative procedure for the production of transgenic animals, know as "Sperm-Mediated Gene Transfer" (SMGT) which is based on the discovery of the capacity of sperm cells to bind and "internalise" exogenous DNA (DNA uptake), transforming them into vectors for the transmission of not just their own genetic material, but also the exogenous DNA of interest.

Advantageously with respect to other transgenic technologies, the procedure summarised above does not require any expensive equipment such as microinjectors or micromanipulators, does not require any delicate operations such as microinjection and the intervention of specialised technical staff. Furthermore, the SMGT procedure has shown itself to be generally effective for a large variety of transgenic animals with variable percentages of genes positively inserted into zygotes and expressed (Lavitrano et al. Mol. Rep. and Dev. 64:284-291, 2003).

Furthermore, the efficacy of the frequency of transfer of the exogenous genes to progeny by means of microinjection in some cases, as for instance in pigs, has not yielded satisfactory results. In addition, it has been observed that the exogenous DNA inserts randomly into the host DNA, occasionally resulting in the blockage or altered transcription of a functional gene. Indeed, the insertion of exogenous DNA sequences occurs by recombination with the host DNA in an entirely random manner, whereby it may even be inserted inside a functional gene sequence, thus completely altering its transcription. Moreover, it has been observed that the integration vectors for DNA molecules undergo the so-called gene "silencing" phenomenon, i.e. no transcription and expression of the genes inserted into the host genome has been detected.

In particular, in seeking to obviate the problem of altered transcription of host DNA, it is necessary to design DNA sequences for insertion or plasmid vectors containing said DNA very carefully and, in any case, there is always a significantly high percentage of cases where it is impossible to predict into which site in the host DNA the exogenous DNA may be inserted, and the consequences this may cause, even to the progeny once it is transmitted to them.

SUMMARY OF THE INVENTION

The problem at the heart of the present invention is hence that of generally providing a method for the insertion of DNA sequences and/or exogenous genetic material inside a host cell in a manner which avoids the above mentioned drawbacks.

This problem is resolved by a method for the insertion of exogenous genetic material into a host cell also male germ cells, in such a manner without interfering with the host genetic material and in such a manner to be transferred to the egg cell and to the deriving embryonic cells unaltered, in accordance with that reported in the enclosed main claim.

A first object of the invention is hence that of providing a method for the safe and reliable insertion of exogenous DNA into a male germ host cell.

A second object of the invention is a method for the fertilisation of an egg cell comprising the use of a sperm cell obtainable in accordance with the first object of the invention.

A third object of the invention is a method for the creation of genetically modified individuals comprising the fertilisation method in accordance with the second object of the invention.

BRIEF DESCRIPTION OF THE FIGURES

Further advantages and characteristics of the present invention will be better understood from the detailed description below, which is given merely by way of non-limiting example, with reference to the enclosed figures wherein.

DETAILED DESCRIPTION OF THE INVENTION

The idea at the heart of the present invention, is that of exploiting the replication and expression capabilities and characteristics of certain DNA plasmid vectors, so as to obtain the corresponding expression and replication of exogenous DNA in a manner that is completely autonomous with respect to the replication and expression of host DNA.

Such capabilities and characteristics have been observed in episomal vectors, which are none other than autonomous, self-replicating circular DNA constructs which are not integrated into host DNA, and thus do not give rise to the aforementioned drawbacks.

Hence, the method in accordance with the present invention comprises the steps of:
  providing an episomal type vector o minichromosome comprising at least one nucleotidic sequence and/or gene sequence of interest which must be transferred into the host and expressed;
  providing vital male germ cells;
  incubating said vital male germ cells treated with said episomal vector, so as to allow the binding of the vector and optionally its entry into the nucleus of the male germ cells.

Characteristics of the Episomal Vector

Episomal vectors can generally be viral and non-viral and offer the advantages of not integrating into the host cell genome, of being capable of self-replication during the host cell cycle, and of segregating into the daughter generations of the host itself.

Preferably, vectors with stable episomal replication have been used which comprise at least one region for anchoring the nuclear scaffold/matrix known as S/MAR (isolated and characterized according to paragraph 23) and acting as an origin of replication of the vector in mammalian cells. Some versions of such vectors also contain the minimal origin derived from the virus SV40 to ensure autonomous replication of the vector. It was subsequently demonstrated that this is unnecessary, since the presence of the S/MAR is sufficient for replication of this class of episomal vectors. In any case, vectors can also comprise a prokaryotic origin of replication (ORI) for replication of the vector in the bacterium *Escherichia coli* and/or viral and/or eukaryotic replication origins. Vectors of this type are described for example by Piechaczek et al. (Nucleic Acids Research, 1999, Vol. 27, No. 2, 426-428).

The S/MAR regions are represented by nucleic acid sequences that are capable of subdividing the chromatin of eukaryotic chromosomes into discrete domains, particularly into topologically connected domains known as loop domains (Luderus, M E et al., 1994, Mol. Cell. Biol., 14, 6297-6305). The domains are bounded by sequences that specifically accumulate in the nuclear matrix or in the nuclear scaffold. These sequences, known as S/MARs are usually several hundreds of base pairs in length and are rich in adenosine and thymine (approx. 70%). Preferred S/MAR sequences for the following invention are those of mammalian origin, more preferably of human origin. These S/MAR sequences are isolated by means of standard procedures (Krawetz, S. A., Draghici, S., Goodrich, R., Liu, Z., Ostermeier, G. C.: In silico and wet-bench identification of nuclear matrix attached regions. Meth. Mol. Med. 2004, 439-458), their structure being characterised (Goetze, S., Gluch, A., Benham, C., Bode, J.: Computational and in vitro analysis of destabilized DNA regions in the interferon cluster. Potential of predicting functional domains. Biochemistry 42, 154-166, 2003). The minimum length of said sequences should be about 800 bp (Jenke et al., PNAS). For example, the particularly preferred sequence has been selected from the 5' region of the human interferon β gene, isolated as a 2.0 kb EcoRI/BglII fragment from the plasmid pTZ-E20 (Bode et al., 1992 Science 255, 195-197) or the 1.7 S/MAR fragment obtained in the polylinker site by means of excision with EcoRI/BglII.

With reference to the sequences of the origin of replication ORI sites, this means sequences of the site for the initiation of replication in prokaryotes, eukaryotes and viruses.

Furthermore, the vectors used are expression vectors, i.e. vectors where a gene encoding one or more proteins or peptides is under the control of gene regulatory sequences that are specific. Said vectors are also endowed with promoters, operators and terminators and ribosomal binding site sequences for correct transcription and translation. Preferably, the vectors have been designed in such a way as not to include any nucleotide sequences for trans-acting replication factors, especially viral, in order to avoid any type of cellular transformation or immune response due to their expression.

Furthermore, the vectors preferably do not contain any nucleotide sequences encoding any viral proteins and, particularly, proteins capable of acting as replication factors in-trans, such as for example the well known SV40 virus "large T antigen" which can act as a tumour inducer and "immortalisation" factor.

The origin of replication (ORI) sites may be selected from those from viral replication sites as EBV-ORI, BPV-ORI or, in particular, SV40-ORI and preferably replication origin sites used for propagation in eukaryotic cells. Obviously, one skilled in the art may modify the vector so as to insert several origins of replication sites according to particular exigencies or preferences.

The episomal vectors used in the invention may furthermore contain one or more antibiotic resistance genes. Their role permits selection, and to check whether the transfection or transformation of the treated cells has occurred or not. Among the most commonly used antibiotics, we may cite by way of example kanamycin, geniticin, gentamicin, ampicillin, tetracycline, streptomycin, spectinomycin, nalidixic acid, rifampicin, chloramphenicol and zeocin.

Figure 1:
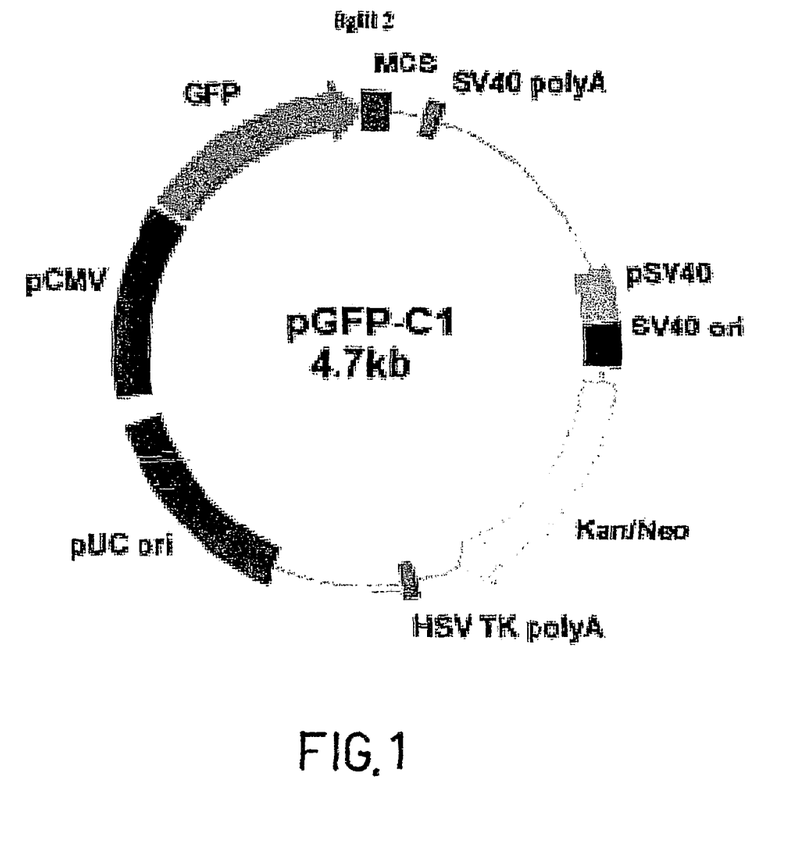
FIG. 1 represents a scheme of the plasmid pGFP-C1.

One particularly preferred type of starting vector is pGFP-C1 (Clontech UK Ltd.) (FIG. 1) wherein the SV40 ORI origin of replication and a nuclear scaffold/matrix anchoring region (S/MAR) sequence isolated and characterized as disclosed on paragraph 23, derived from the 5' region of the human interferon β gene isolated from plasmid pTX-E20 as a 2 kb EcoRI/

Figure 2:
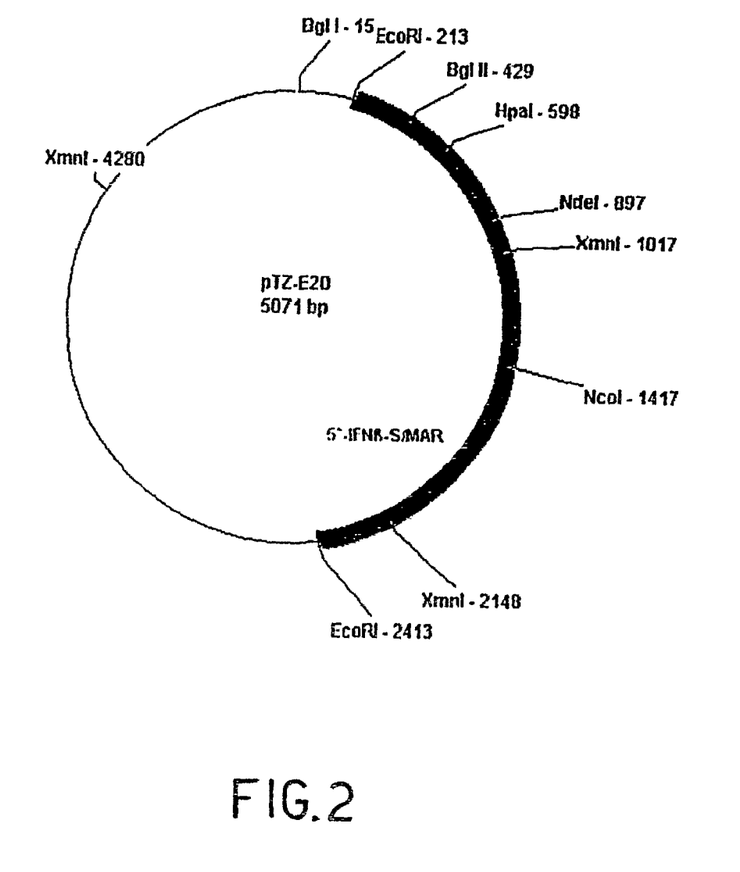
FIG. 2 represents a scheme of the plasmid pTX-E20.
Figure 3:
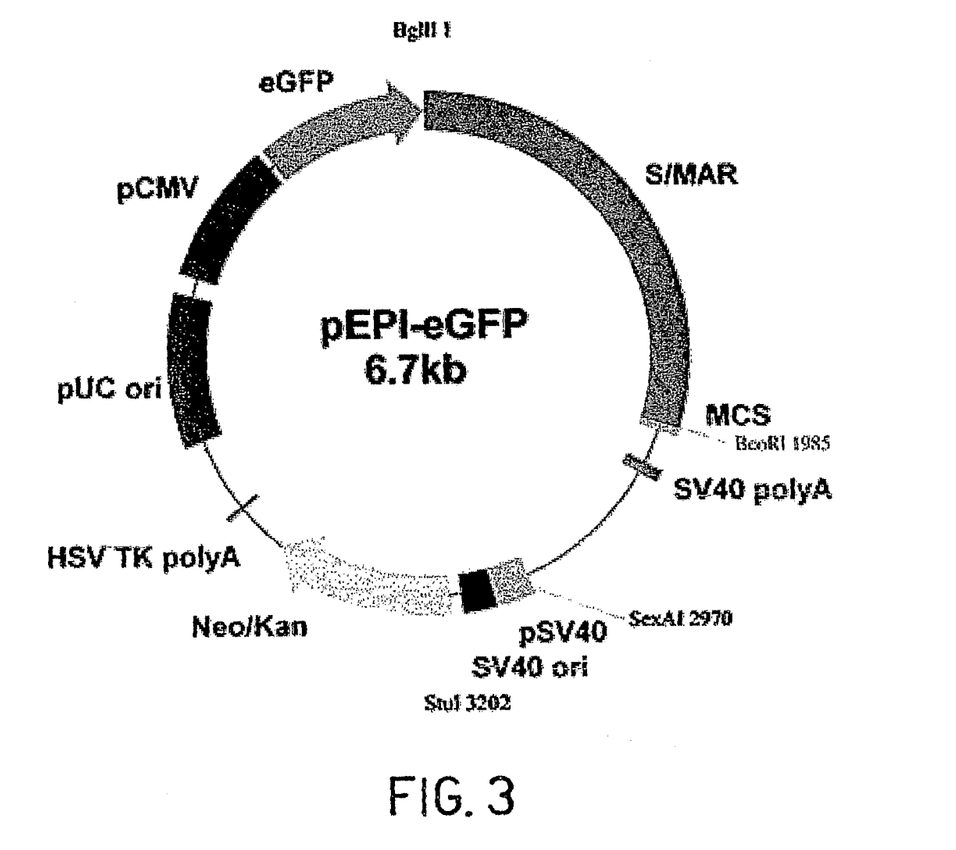
FIG. 3 represents a scheme of the episomal plasmid vector pEPI-eGFP.

BglII fragment, have been inserted (FIG. 2). The restriction map of the resulting plasmid PEPI-1 is shown in FIG. 3 (Piechaczek et al., Nucleic Acids Research, 1999, Vol. 27, No. 2, 426-428; Glover et al., Nature Reviews Genetics, published on line 10 Mar. 2005).

Moreover, other suitable derivatives of PEPI-1 that can be used according to the present invention are represented by pEPI-RSV, pDiMAR, pTetMAR, pMAR, as disclosed in Jenke et al. (Nuclear scaffold/matrix attached region modules liked to a transcription unit are sufficient for replication and maintenance of a mammalian episome, Methods, PNAS, Aug. 3, 2004, vol. 101, no. 31).

It should be pointed out that the modifications made to the commercial plasmid pGFP-C1, or other analogous starting plasmids, in order to obtain the plasmid of interest have been performed in accordance with molecular biology techniques which are widely known in the art (Maniatis et. al, 1982, *Molecular Cloning, A Laboratory Manual*, Cold Spring Harbor Laboratory, Cold Spring Harbor, N.Y.) whereby they will not be gone into in any further detail here.

In addition, the vector of the invention may include promoter elements which may be represented by suitable promoters inserted in the 5' end including constitutive, cell cycle specific, tissue specific, metabolically regulated or inducible promoters or "enhancers".

The genes of interest which may be inserted in the episomal vector comprise genes encoding proteins of therapeutic interest, such as for example the gene hDAF (human decay accelerating factor), or genes which develop certain host conditions for the purposes of research.

The episomal vectors just described may also be used for transfection into sperm cells in association with coadjuvants, stabilisers and substances which promote transfection. Furthermore, special vectors, known as transfection vectors, which promote transfection when used in combination with the episomal vectors, may be used.

In accordance with a particularly preferred embodiment of the invention, the episomal vectors may be included inside carriers, for example pharmaceutical type carriers such as liposomes, so as to further increase the level of transfection thanks to the barrier protecting against DNAse action.

Furthermore, the liposome-episomal vector complex may include nucleic acid binding proteins such as for example, HMG chromosomal proteins or histones such as H2A, H2B, H3 with the advantage that expression of the integrated gene of interest may be increased.

Similarly, histidine containing polypeptides may be used in order to increase the ease of the passage across the plasma membrane and hence entry into the host cell, while anchoring of the vector to the liposome may be achieved by means of the use of a C-terminal cystein.

According to an embodiment of the invention, alternatively to the use of episomal plasmid vectors human artificial choromosomes (HACs) can be used. These structures are represented by constructions of DNA molecules that resemble natural chromosomes in that they are capable of replication and retention at low, defined copy number within host cells (Glove et al., Nature Reviews Genetics, published on line 10 March 2005). An example of these chromosomes are described in Ebersole et al. (Mammalian artificial chromosome formation from circular alphoid input DNA does not require telomere repeats Hum. Mol. Genet 9, 1623-1631, 2000).

A particular approach for the creation of HAC involves truncation of mammalian chromosomes down to mitotically stable minichromosomes of 1-10 Mb consisting of Alpha-satellite arrays (Farr et al., Generation of human X-derived minichromosome using telomere-associated chromosome fragmentation EMBO J. 14, 54444-5454 1995; Heller et al., Minichromosomes derived from the human Y chromosome by telomere directed chromosome breakage, Proc. Natl. Acad. Sci. USA 93, 7125-7130, 1996). DNA alfa-satellite are a class of about 170 bp repeating sequences of nucleotide pairs found at centromeres.

Description of the Construction of the Episomal DNA

The vector production method in accordance with the previously mentioned points, comprises the separation of a region from plasmids or other nucleic acid sequences and the insertion or ligation into a plasmid vector by means of restriction enzymes. In greater detail, the method comprises the substitution of one or more sequences encoding replication factors into an original vector with at least one S/MAR region isolated and characterized as disclosed on paragraph 23. This operation may be carried out using conventional molecular biology techniques, providing the excision of said original regions using restriction enzymes, and the insertion of the S/MAR fragments into the vector.

All the genetic elements described above may be inserted into the episomal vector in accordance with molecular biology methods widely known to those skilled in the art (Maniatis, T., Fritsch, E. F. & Sambrook, J. (1982) *Molecular Cloning, A Laboratory Manual*, Cold Spring Harbor Laboratory, Cold Spring Harbor, N.Y.).

Description of the "Sperm-Mediated Gene Transfer" (SMGT) Procedure

Once the episomal vector, as described previously, is made available, it is necessary to optimally prepare the male germ cells so that they may receive and efficiently pass-on said vector.

The male germ cells can be collected during any moment of their maturation starting from spermatogonium.

Preferably, the procedure used in accordance with the present invention generally comprises a first step of harvesting the sperm cells, and a second step of selecting the sperm cells on the basis of the percentage of cells endowed with motility with respect to the total cells harvested. Indeed, the SMGT procedure is based on the optimisation of two groups of parameters, represented by the quality of the sperm sample and the capacity to take up the DNA (DNA uptake). In particular, sperm cells are suitably selected so as to show a motility percentage, after taking from the individual, of at least 70% and not less than 65% after washing to remove sperm fluid.

Sample Quality

Sample quality has been evaluated using standardised parameters for evaluation of sperm boar such as the volume without gelatinous mass (>100 ml), the concentration (>1× $10^6$ spermatozoa/ml), the presence of any anomalous sperm cells (<20%) and the motility at the time of harvesting (>65%). Particularly, percentage motility has been evaluated in accordance with the procedure described by Lavitrano et al., Mol. Repr. and Develop. 64:284-291, 2003 (Evaluation of Semen Quality).

Preferably, sperm cells have been harvested and separated by discarding the first ejaculate fraction, low in spermatozoa content, and collecting more or less the initial 30-40% of the second ejaculate fraction, richer in spermatozoa but with low seminal fluid content. Furthermore, the selected ejaculate may advantageously be harvested and kept at a temperature of 37° C. in pre-warmed, sterile containers.

DNA Binding and Uptake Capacity

The harvested fraction is then treated so as to completely remove the seminal fluid. Particularly, said removal step may take place by means of at least a washing step using a suitable liquid, preferably preceded by a removing step of the gelling portion of the ejaculate carried out for example passing through sterile gauze.

Preferably, removal of the seminal liquid comprises the following steps in sequence:
a) bringing the ejaculate sample into contact with a suitable wash medium, so as to dilute the sample;
b) separating said sample from the wash medium;
c) bringing said sample once again into contact with said wash medium;
d) once again separating the sample from the wash medium.

Following step a) the diluted sample may be advantageously incubated for several minutes, for example from 3 to 10 minutes, preferably 5 minutes, to promote the action of the wash medium.

The separation step b) may be accomplished in any way known in the art, preferably by means of centrifugation. Centrifugation may be carried out for example at from 400 g to 1000 g, preferably at 800 g, at a temperature of between 16° and 38° C., preferably at 25° C. for a period of time of between 3 minutes and 20 minutes, preferably 10 minutes.

Once the supernatant from step b) has been eliminated, the pelleted sperm cells are resuspended in the so-called wash medium and the separation step d) may be carried out under the same conditions as described for step b). Preferably, centrifugation is carried out at a temperature of 17° C.

Particularly, the wash medium may be an aqueous composition comprising glucose, at a concentration of between 56 to 69 mM, sodium citrate, at a concentration of between 31 to 37 mM, EDTA, at a concentration of between 11 to 14 mM, citric acid, at a concentration of between 14 and 17 mM and Trizma base, at a concentration of between 48 to 59 mM. The final osmolarity of the medium should typically be between 200 and 320 mOs, while the pH is adjusted using for example HCl from 6.6 to 7.5, preferably 6.8.

Preferably, the aforementioned wash medium may be sterilised for example in an autoclave or by means of microfiltration, and pre-warmed to a temperature of 37° C. prior to use.

It should be noted that in accordance with one particularly preferred embodiment, the wash medium is calcium-free in order to avoid that this may promote/stimulate any endogenous endonuclease activity and, consequently, have a deleterious effect on the episomal vector.

Furthermore, the wash medium may include BSA at a concentration of between 1 g/l and 30 g/l or any other protein source suitable for the survival of the sperm cells.

As disclosed above, the medium pH is adjusted to a value comprised between 6.6 and 7.5. Preferably, pH is 6.8 because it has been observed a significant increase of DNA uptake with said pH value.

Procedure for the Uptake of the Episomal Vector into the Sperm Cells (DNA Uptake)

Once the episomal vector and the sperm cells have been provided in accordance with the points described above, the subsequent step consists of bringing the vector into contact with the sperm cells, so that the vector binds the cells and optionally enters the nucleus of said cells or, in other words, transfection of the sperm cells with the episomal vector occurs.

It has been observed that in order to obtain the best vector "internalisation", at least $1 \times 10^6$/ml, preferably at least $1 \times 10^9$, sperm cells are incubated with from $10^{-2}$ µg to 100 µg of episomal vector, preferably 5 µg/$10^8$ spermatozoa/ml. The incubation time is generally comprised of between 30 minutes and 4 hours, and the temperature may vary from 17° to 38° C.

Furthermore, addition of the vector should preferably occur within 60 minutes from the sperm cells being washed, more preferably within 30 minutes.

Procedure for the Creation of Genetically Modified Animals

As already mentioned in the introduction to this description, at this point, the sperm cells, transformed in accordance with the invention, may be used to fertilise an egg cell, and make it such that the resulting zygote develops into a genetically modified individual. The procedure comprises the following steps in sequence:
i) bringing a sperm cell, modified in accordance with the previously described method, into contact with an egg cell, in order to permit its fertilisation and
ii) maintaining the zygote resulting from the fertilisation under such conditions as to allow the development of the individual.

Fertilisation is preferably performed by means of widely known in vivo artificial insemination techniques such as for example the laparoscopic technique (Fantinati et al., 2005).

A further subject of the present invention is a non-human genetically modified individual, the germ and somatic cells of which contain a stable episomal expression vector, as described above. In particular, this individual is a mammal, preferably a pig.

An embodiment of the invention, given purely by means of non-limiting example is reported hereinafter.

Materials and Methods

Plasmid Vectors

The plasmids used in this study were pEPI-eGFP and the commercial plasmid pGFP-C1 (Clontech UK, Ltd.) from which the pEPI vectors are derived. A map of both plasmids is given in FIGS. 3 and 1 respectively, that show where the two plasmids differ: pEPI-eGFP contains a 1.7 kb S/MAR, isolated and characterized as disclosed on paragraph 23, obtained from the human interferon β-gene in the polylinker site; pGFP-C1 contains the GFP gene, whereas pEPI-eGFP has the enhanced version of the gene, eGFP, in the same location. All the other sequences of the two plasmids are identical. The plasmids were amplified in *Escherichia coli* NovaBlue (Novagen-Calbiochem).

Animals

Semen was collected from a trained Large White boar that had abstained for 3 days. Large White recipient prepubertal gilts (99±1.80 kg), were superovulated and synchronized by an intramuscular (im) injection of eCG (1250 IU) (Folligon® Intervet International B. V., Boxmeer, The Netherlands) followed 60 hours later by hCG (750 IU). Ovulation was expected 40-44 hr after hCG. Surgical laparoscopic insemination at the utero-tubal junction ($1 \times 10^9$ DNA treated sperm/gilt) was performed 36 hours after hCG injection as previously described (Fantinati et al., 2005). Animal care and experimental procedure met local, national, and European Union Guidelines.

Preparation of Sperm

Semen was collected and prepared as reported previously (Lavitrano et al., 2002; Lavitrano et al., 2003) with minor modifications. Briefly, immediately after collection semen was diluted 1:1 with Swine Fertilisation Medium (SFM) (11.25 g Glucose, 10 g Sodium Citrate ($2H_2O$), 4.7 g EDTA ($2H_2O$), 3.25 g Citric Acid ($H_2O$), 6.5 g Trizma per liter, adjusted to pH 6.8) prewarmed to 37° C. Seminal fluid was removed by diluting again sperm suspension 1:10 with SFM and centrifuging it in 50 ml Falcon tubes (Becton & Dickinson, Milano, Italy) (800×g for 10 min). The washing procedure was repeated again with SFM supplemented with 6 g/l of BSA Fraction V (Sigma-Aldrich, Milano, Italy) (SFM/BSA) prewarmed to 25° C. Sperm cells were counted using a hemocytometric chamber and resuspended at a working dilution of $1 \times 10^8$ cells/ml in 25° C. SFM/BSA.

Sperm-DNA Uptake

The sperm was taken from a single trained boar previously selected based on standard parameters used in conventional animal breeding programs (volume, sperm concentration, presence of abnormal sperm cells, and motility) and on the ability of the sperm cells to take up exogenous DNA. DNA uptake by sperm was assessed by time course experiments. Liquid scintillation counting was performed on washed ejaculated sperm cells (Lavitrano et al., 2003) resuspended at a concentration of $1 \times 10^8$ cells/ml SFM/BSA, mixed with 5 µg pEPI-eGFP and pGFP-C1 plasmid DNA labeled by nick translation (Maniatis). Parallel time course experiments were performed at different temperatures (17, 20, 25, 37° C.). Increasing amounts of DNA (50, 100, 200, 400, 800 ng) were utilized to determine the most appropriate sperm-DNA incubation conditions. Aliquots containing $1 \times 10^6$ sperm cells were withdrawn from the incubation mixture at specific times, diluted in Eppendorf tubes containing 1 ml of SFM and washed twice by centrifuging at 1,250 g for 5 min in a microfuge.

Sperm/DNA Uptake for SMGT and Laparoscopic Insemination

Washed sperm cells were incubated for 1 h at 17° C. with non-linearized pEPI-eGFP vector (5 µg DNA/ml/$10^8$ spermatozoa). The tube was inverted every 20 min to prevent sperm sedimentation. The final 20 min of incubation was at RT with heating (37° C.) for 1 min before laparoscopic insemination (Fantinati et al., 2005). Synchronyzed gilts were laparoscopically inseminated with 5 ml aliquots per uterine horn, containing $5 \times 10^8$ DNA-treated spermatozoa. Surgical harvest of fetuses was performed under total anesthesia after 70 days of pregnancy. Specimens of different organs were collected for further analysis.

RT-PCR Analysis

Total RNA was extracted by Tissue kit (Versagene™ RNA, Gentra). Of the total RNA, 2 µg were reverse-transcribed using SuperScript III (Invitrogen). The cDNA obtained was amplified with the following primers (Sigma-Genosys), pEPI-1: 5'-CCT GAA GTT CAT CTG CAC CA-3' (forward), 5'-TGC TCA GGT AGT GGT TGT CG-3' (reverse). PCR products were analysed on 1.5% agarose gels stained with ethidium bromide. The RT-PCR experiments were subjected to the routine controls. The primers used amplified a 480 Kb fragment. The risk of contaminating genomic DNA coamplification was ruled out by running the PCR reaction without prior reverse transcription.

Preparation of DNA and Southern Blot Analysis

Extrachromosomal DNA from a HIRT extract (Piechaczek, 1999) prepared from tissue sections was isolated and analysed. Briefly, tissues were lysed with 6 ml of a 1:1 mix of TEN (1 mM EDTA/150 mM NaCl/10 mM Tris HCl, pH 7.5) and HIRT (1.2% SDS/20 mM Tris HCl, pH 7.5/20 mM EDTA) solutions. Twenty minutes later tissues were dounce homogenized on ice. A 0.1 volume of NaCl 5 M was added and the tissues were incubated overnight at +4° C. Samples were centrifuged (30 min., +4° C., 6000 rpm) and supernatants were recovered. DNA was first purified with phenol and subsequently with phenol:chloroform:isoamyl alcohol (25: 24:1) and chloroform:isoamyl alcohol solutions (24:1). DNA was precipitated overnight at −20° C. after addition of 0.1 volume of 3M sodium acetate and 2.5 volumes of ethanol. DNA was recovered by centrifugation and resuspended in 0.1× TE (TE: 1 mM EDTA/10 mM Tris HCl, pH 7.5). HIRT-extracted DNA (20 µl), both undigested and Bgl II digested, was fractionated on 0.7% agarose gels, and blotted onto nylon membranes (Southern, 1975). pEPI-eGFP vector was labeled with $^{32}$P (Ready-to-Go labeling kit, Amersham Pharmacia) and used as a probe. Hybridisation was carried out in Church buffer (0.25 M sodium phosphate buffer, pH 7.2/1 mM EDTA/1% BSA/7% SDS) at 65° C. for 16 hours. Under our stringency conditions, we observed no hybridisation in DNA samples from control fetuses.

Rescue Experiments

Transformation of E. coli with DNA prepared by Hirt extraction was performed according to HIRT B (1967, Selective extraction of polyoma DNA from infected mouse celle cultures, J. Mol. Biol.; 26(2):365-369). Transformed colonies were selected on agarose plates containing 30 µg/ml kanamycin. DNA was isolated from individual resistant clones and subjected to restriction analysis.

Confocal Microscopy

Biopsies of different organs were fixed with 4% paraformaldehyde (Sigma-Aldrich, Milan, Italy) in 0.01 M phosphate-buffered saline, pH 7.4 (PBS) at 4° C. for 2 hours, thoroughly washed in PBS, at 4° C. overnight, then embedded in OCT Matrix (CellPath, Hemel Hempstead, UK) and quickly frozen in chilled isopentane in dry ice. 30 µm Cryostat sections were cut and mounted on chrome-alum gelatin-coated slides, left to dry in a dust free cooled cabinet, coverslipped and sealed with Vectashield (Vector Labs, Inc. USA). Slides were analysed with a Zeiss Axioskope 2 epifluorescence microscope (Zeiss, Germany), equipped with a high-resolution digital camera (C4742-95, Hamamatsu Photonics, Milan, Italy) and HiPic software (Hamamatsu Photonics, Germany). The expression of the fluorescent protein "Aequorea Victoria" variant GFP (6083-1) was imaged using the 09 Zeiss Filter set composed of a BP 450-490 excitation filter, a FT 510 beamsplitter, and a LP 515 emission filter on light path; the signal was coded as green. Images were adjusted for brightness and contrast and assembled as plates using Adobe PhotoShop (v. 6.0; Adobe Systems, San Jose, Calif.). Analysis of expression was accomplished by a computer assisted image analysis system (MCID 7.0; Imaging Res. Inc, Canada). To analyse protein expression we measured GFP signals as counts/area and as positive cells/counted area. These values express respectively the number of fluorescent dots relative to the fixed scanned area and the percentage of positive cells. The averages were obtained from six randomly selected sections for each sample, and comparisons were made between genetically modified and control samples. All data were exported and converted to a frequency distribution histogram using the Sigma-Plot 8.0 program (SPSS-Erkrath, Germany). A paired t-test was used to compare genetically modified animals and controls. A difference was accepted as significant when the probability was less than or equal to 5% ($p<0.05$). All data are expressed (signal/µm$^2$) as means±S.E.M. (P7:145±40; P11: 180±17; P13:120±7), as depicted in FIG. 8.

Results

Figure 4A:
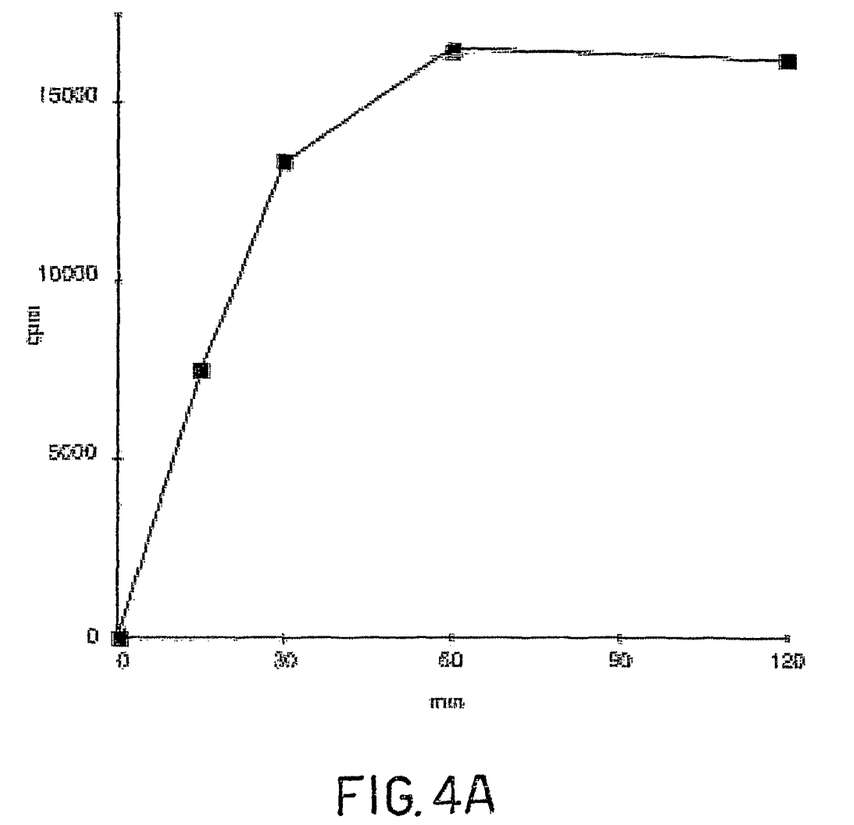
FIGS. 4A and 4B represent a time-course experiment of the uptake of nick translated pEPI-eGFP and pGFP-C1 circular plasmids.
Figure 4B:
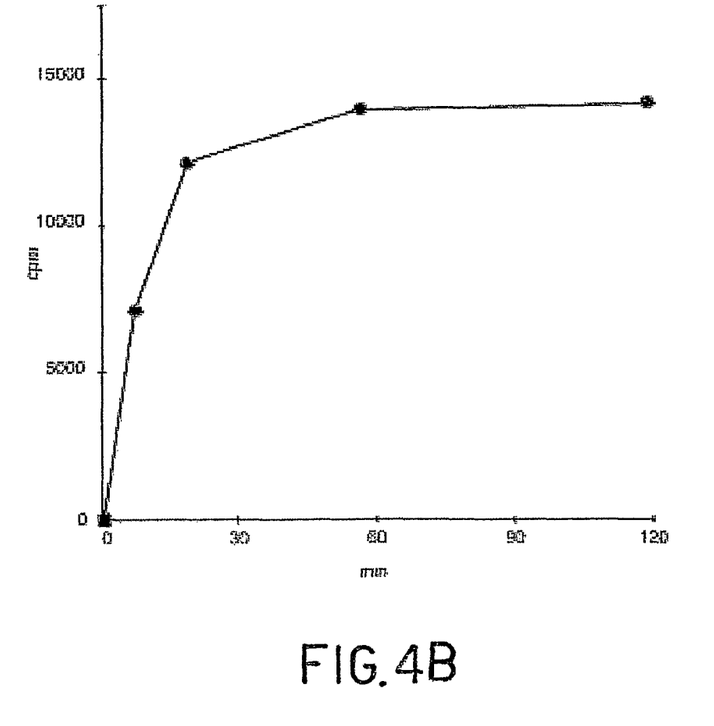

Donor Selection and Sperm-DNA uptake. Selection of sperm donor and optimization of DNA uptake are the key steps in the successful outcome of SMGT (Lavitrano et al., 2003). Large White boar was used as sperm donor. Semen quality was assessed by standard procedures used in conventional animal breeding programs (see Methods) and DNA uptake was assessed by liquid scintillation counting in time course experiments using suitably labelled pEPI-eGFP and pGFP-C1 plasmids. FIGS. 4A and 4B show a time-course of uptake of nick translated pEPI-eGFP (FIG. 4A) and pGFP-C1 (FIG. 4B) circular plasmids by ejaculated pig sperm cells. The kinetics of uptake of the two plasmids was similar. In both cases there is rapid binding of most of the DNA during the initial 15-30 min, followed 60 min later by a plateau.

Figure 5A:
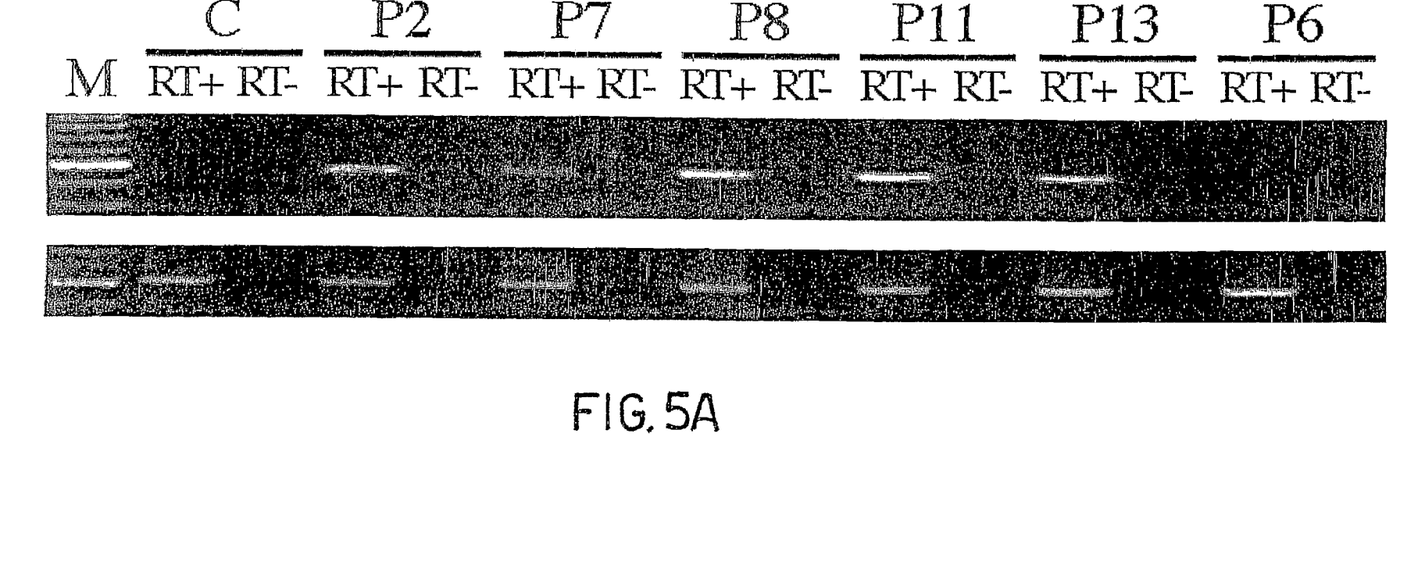
FIGS. 5A and 5B represent the RT-PCR_result using RNA from liver, muscle and heart of foetuses.
Figure 5B:
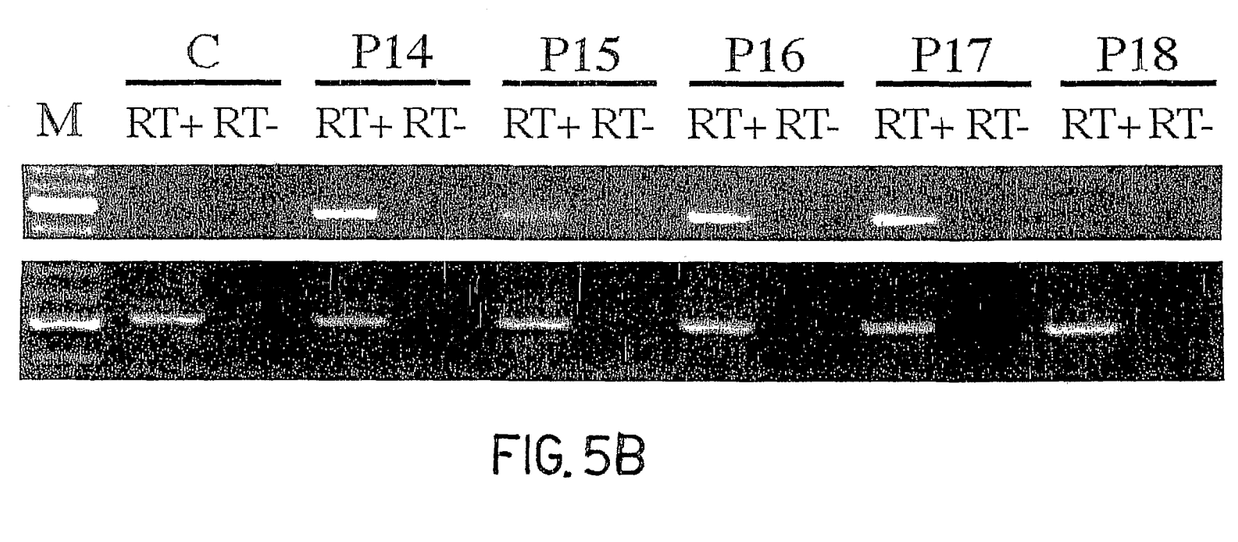

Parallel time-course experiments were performed at different DNA concentrations and temperatures to determine the best DNA incubation conditions for sperm cells from the selected boar (data not shown). The results obtained suggested that the optimal conditions were a DNA concentration of 5 μg of plasmid DNA for $10^8$ spermatozoa per ml at 17° C. for 1 h. Sperm cells from the selected boar were used as vectors for transferring the non-viral episomal vector pEPI-eGF into eggs by laparoscopic insemination (Fantinati et a., Theriogenology, 2005). Eighteen fetuses were harvested from two sows (8 and 10 fetuses, respectively) after 70 days of pregnancy (more than ⅔ of the pregnancy period) when organogenesis was fully completed. A further 5 fetuses were produced by a fertilisation performed with sperm that had not been incubated with exogenous DNA (negative controls). Tissue sections were recovered from kidney, liver, heart, lung and muscle of fetuses obtained from all three fertilisations and studied for presence and expression of the report transgene. The pEPI-eGFP vector is expressed in tissues of genetically modified pigs. Expression of the eGFP reporter gene was assessed by RT-PCR analysis. Total RNA was prepared from various tissues of all 18 animals and tested for the presence of the eGFP transcript. FIGS. 5A and 5B depict examples of such an RT-PCR analysis using RNA from liver (FIG. 5A) and muscle and heart (FIG. 5B) of fetuses P6, P7, P8, P11, P13, P9 (FIG. 5A) and P14, P15, P16, P17, P18 (FIG. 5B). In FIG. 5, M symbol indicates the marker of molecular weight; symbols RT+ or RT– indicate that amplification reaction has been carried out on template previously obtained in the retrotranscription reaction respectively in presence or in absence of retrotranscriptase enzyme; C indicates negative control, i.e. not genetically modified animal tissue. Primers used were derived from the eGFP gene and amplified a 480 bp fragment. In no case was a PCR product amplified using RNA from fetuses control tissue (FIG. 5A, lane 1, 2; FIG. 5B, lane 1, 2). The eGFP transcript was present in at least one tested tissue in 9 out of 20 tested fetuses. In one fetus the presence of this transcript could be demonstrated in all tissues analysed, whereas in the other fetuses the transcript was present on average in between 1 out 4 to 3 out of 4 tested tissues. The eGFP transcript was present in 50% of all livers tested, in about 27% of muscle, in 27% of heart and in 16% of kidneys tested.

Figure 6A:
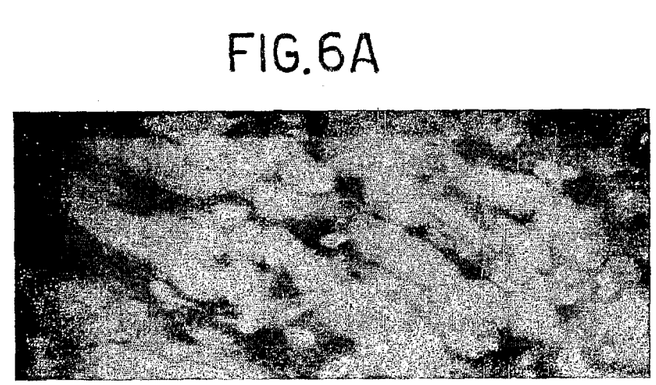
FIGS. 6A-6D represent histologic analysis of muscle tissue from different animals.
Figure 6B:
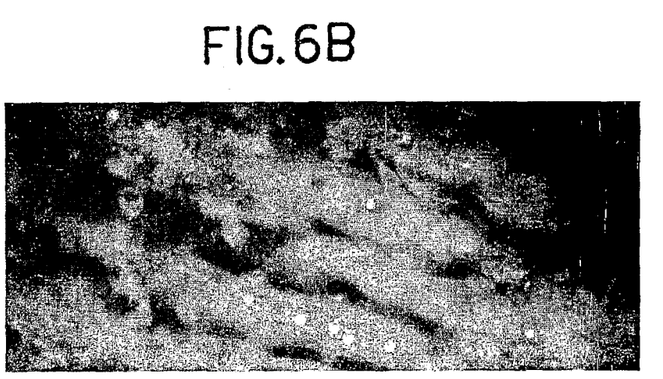
Figure 6C:
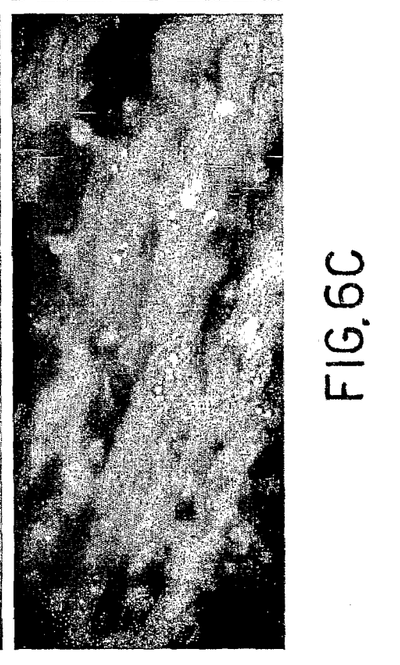
Figure 6D:
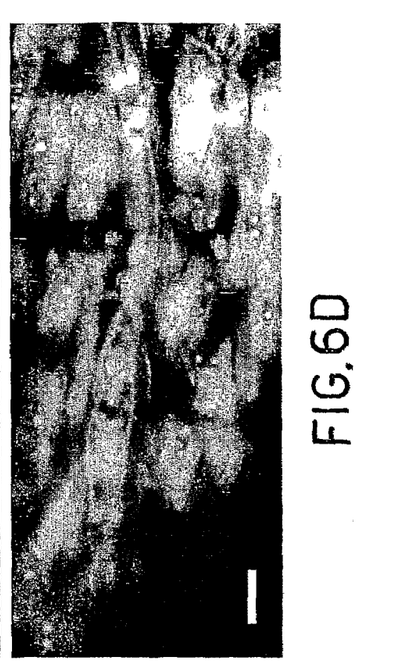
Figure 6E:
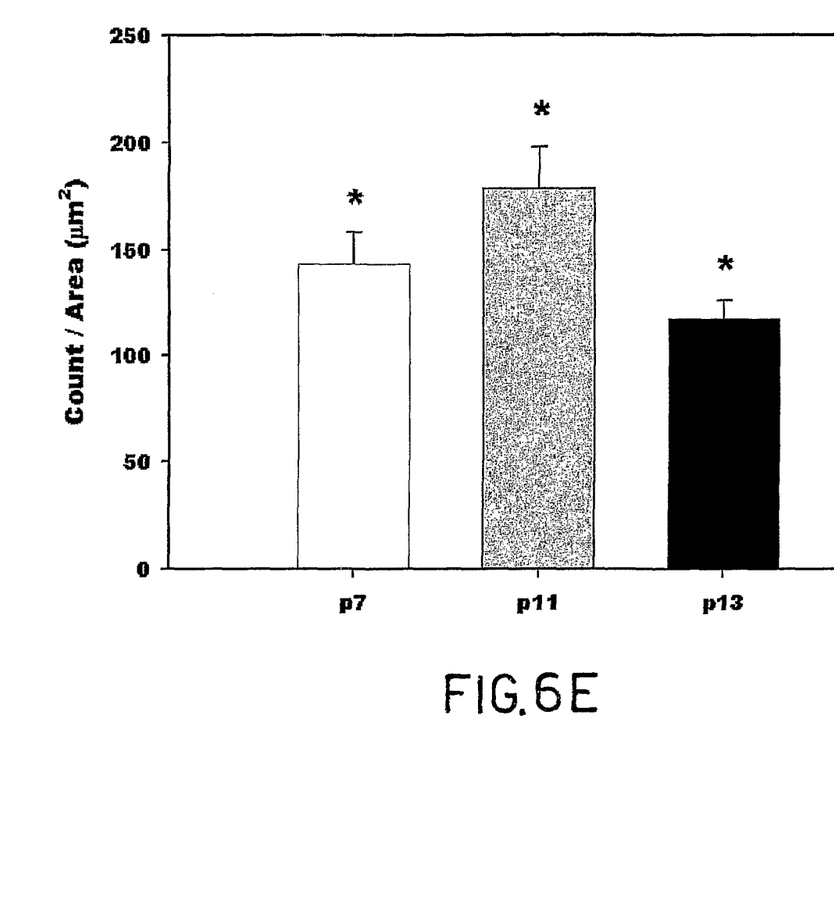
FIG. 6E represents an histogram of distribution frequency of fluorescent points with relation to fixed, scanned area and related to the expression of the GFP variant fluorescent protein "Aequorea Victoria" in some samples.

Expression of the eGFP protein was analysed by confocal microscopy in muscle tissues from 8 fetuses (P6-P13) supposed genetically modified and from control fetuses. eGFP expression could be demonstrated in 5 (P7, P8, P11, P13 and P6) out of 8 tested fetuses. eGFP protein expression could be shown in all 5 fetuses that had tested positive for the presence of the eGFP transcript, as demonstrated by RT-PCR, while no eGFP transcript had been previously found in the other three fetuses. Three fetuses positive for eGFP protein expression and 3 control fetuses were chosen for quantitative evaluation of eGFP expression. Histological analysis of muscle tissues from the different animals displayed fibers of normal appearance (FIG. 6A). eGFP protein expression could be seen in between 62% and 83% of the cells (FIG. 6b-6D). The analysis of fluorescence emission revealed discrete expression of a fluorescent protein in the fibers, appearing as discrete intense fluorescent dots (FIGS. 6B and 6D). The level of protein expression was not identical in all fetuses although it was in the same range of values, between about 117 and 179 fluorescent spots per area (FIG. 6E). No fluorescent spots could be detected in muscle tissue from control fetuses (FIG. 4A).

Figure 7A:
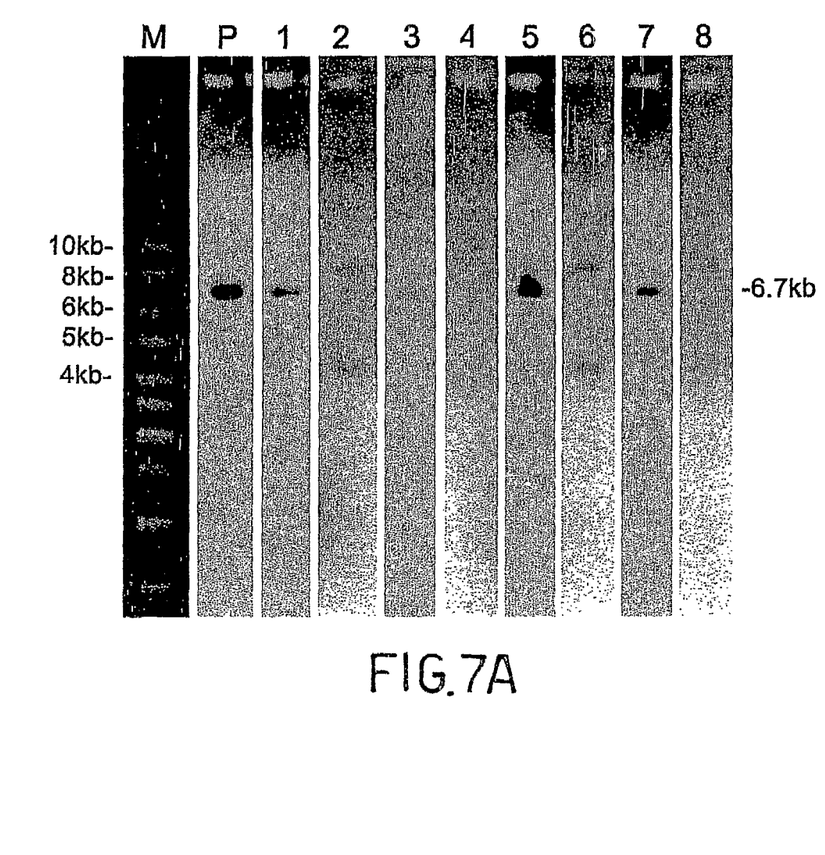
FIGS. 7A and 7B represent extracromosomic DNA analysis obtained by Hirt extraction (Hirt, 1967) subjected to Southern Blot (7A) and to restriction enzymatic analysis (7B).
Figure 7B:
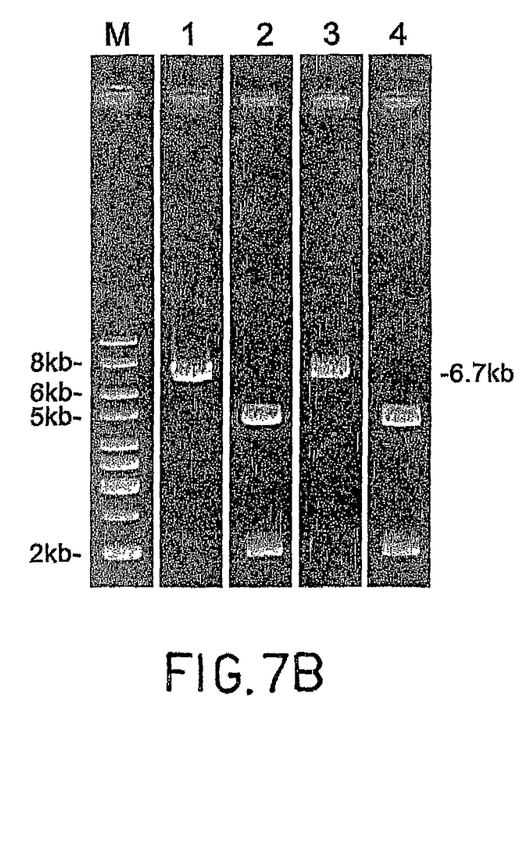

The pEPI vector is maintained in the episomal state. To determine whether the non-viral vector used to genetically modify pigs by SMGT was retained in the fetuses as an episome, DNA was extracted by the Hirt method (Hirt, 1967) from liver (P11, P15), muscle (P14) and kidney (P15) tissues of three fetuses. DNA samples, either undigested or digested with BglII, were fractionated on agarose gels, Southern blotted, and hybridised, using the entire plasmid as a probe. DNA bands were observed in all samples tested and the DNA pattern was always identical: in undigested DNA samples two different bands, corresponding respectively to open circle, linear and supercoiled forms of the vector, were observed (FIG. 7A); in Bgl II digested DNA samples one band, corresponding to the linearized form of the plasmid, was found. In FIG. 7A, M symbol indicates molecular weight marker; P symbol indicates BglII digested plasmid; numbers 1 and 2 correspond to DNA analysis extracted with Hirt from P11 sample liver respectively linearized (1) and not digested (2); 3 and 4 numbers correspond to DNA analysis extracted with Hirt from muscle of P14 sample respectively linearized (3) and not digested (4); numbers 5 and 6 correspond to DNA analysis extracted with Hirt from P14 sample kidney respectively linearized (5) and not digested (6); numbers 7 and 8 correspond to the DNA analysis extracted with Hirt from P15 sample liver respectively linearized (7) and not digested (8). The intensity of these bands was very weak and by comparing it to the hybridisation of isolated vector DNA at different concentrations, it was estimated that copy number of the vector present in transfected cells must be below 20 copies per cell (data not shown), a number observed for various cell lines transfected with this vector (Piechaczek, Schaarschmidt, Athanassiou). In no case hybridisation to high molecular weight genomic DNA was observed. The analyses of Hirt-extracted DNA suggested that the pEPI-EGFP plasmid was present in the extrachromosomal DNA fraction. The episomal state was further confirmed by rescue experiments in which E. coli was transformed with DNA isolated from a Hirt-extract from these tissues. Kanamycin resistant bacterial colonies were obtained from liver (P11, P15) and muscle samples (P14) although, due to the low copy number of the vector, only very few (between 3 and 10) colonies were obtained in these rescue experiments. Plasmid DNA extracted from these clones were digested with Bgl II or with BglII and EcorI (double enzymatic digestion) and analysed on agarose gels. In all cases the restriction patterns were identical to the ones observed in the digestion of pEPI-EGFP plasmid (FIG. 7B). In FIG. 7B, M symbol indicates molecular weight marker; numbers 1 and 2 indicate respectively pEPI-eGFP linearised with BglII or digested with BglII and EcorI; 3 and 4 numbers indicate respectively plasmidic DNA extracted from colonies obtained from P11 sample liver, respectively linearised with BglII or digested with BglII and EcoRI.

The invention claimed is:

1. A method for the transfer of nucleotide sequences and/or exogenous genes into animal cells comprising the following steps in sequence:

providing an episomal type vector comprising at least one nucleotide sequence and/or gene sequence of interest which must be transferred into, and expressed in the host;

providing vital male germ cells; and incubating the vital male germ cells with the episomal vector to allow binding of the episomal vector with the cells and optionally entry of the episomal vector into the nucleus of the vital male germ cells, wherein providing vital male germ cells comprises
selecting sperm cells, having a motility percentage over the total, of at least 70% at the time of harvesting and removing seminal fluid from the selected sperm cell to maintain a motility percentage of not less than 65%;
wherein the removing comprises:
bringing the selected sperm cells into contact with a suitable wash medium to obtain a first diluted sample
separating the first diluted sample from the wash medium to obtain a first separated sample;
bringing the first separated sample into contact with the wash medium to obtain a second diluted sample;
separating the second diluted sample from the wash medium to obtain a second separated sample;
wherein the first diluted sample is incubated for 3-10 minutes; and
wherein the wash medium is a composition comprising glucose, at a concentration of between 56 and 69 mM, sodium citrate at a concentration of between 31 and 37 mM, EDTA at a concentration of between 11 and 14 mM, citric acid at a concentration of between 14 and 17 mM and Trizma base at a concentration of between 48 and 59 mM, the final osmolarity typically being between 200 and 320 mOs and the pH being adjusted from 6.6 to 6.8.

2. The method according to claim 1, wherein the episomal vector is a stable episomally replicating vector comprising at least one nuclear scaffold/matrix anchoring region (S/MAR) and at least one viral, procariotic and/or eucariotic replication origin (ORI).

3. The method according to claim 2, wherein the S/MAR regions are of mammalian origin, preferably human and have a minimum length of 800 bp.

4. The method according to claim 3, wherein the S/MAR region is selected from the 5' region of the human β interferon gene, isolated as a 2.0 kb EcoRI/BgIII fragment from the plasmid pTZ-E20 or the 1.7 S/MAR fragment obtained in the polylinker site.

5. The method according to claim 2, wherein said origin is selected from EBV-ORI, BPV-ORI and SV40-ORI.

6. The method according to claim 1, wherein the vector is an expression vector.

7. The method according to claim 1, wherein the vector further comprises one or more of the following gene elements: a promoter, an operator, a terminator and ribosomal binding site sequences.

8. The method according to claim 1, wherein the vector is, in addition, free of any nucleotide sequences encoding any viral proteins, above all if acting in trans.

9. The method according to claim 1, wherein the vector further comprises one or more antibiotic resistance genes.

10. The method according to claim 1, wherein the vector further comprises constitutive, cell cycle-specific, tissue-specific, metabolically regulated or inducible promoters or enhancers.

11. The method according to claim 1, wherein the gene of interest carried by the vector is a gene encoding a protein of therapeutic interest.

12. The method according to claim 1, wherein the vector is included inside a liposomal carrier.

13. The method according to claim 12, wherein the vector is bound to the carrier by means of nucleic acid binding proteins.

14. The method according to claim 12, wherein the carrier comprises histidine-containing polypeptides in order to increase the ease of entry into the host cell.

15. The method according to claim 1, wherein the vector is circular plasmid pEPI-1 or a derivative thereof selected from the group consisting of pEPI-RSV, pDiMAR, pTetMAR and pMARS.

16. The method according to claim 1, wherein the selecting comprises harvesting sperm cells from an ejaculate and identifying a percentage motility of the harvested sperm cells.

17. The method according to claim 16, wherein the harvesting comprises collecting 30-40% of a second ejaculate fraction in sterile containers, pre-warmed to a temperature of 37° C.

18. The method according to claim 1, wherein separating the first diluted sample is accomplished by centrifugating the first diluted sample at a speed of between 400 g to 1000 g, at a temperature of between 16° and 38° C. for a period of time comprised of between 3 minutes and 20 minutes.

19. The method according to claim 1, wherein the wash medium is sterilised and pre-warmed prior to use.

20. The method according to claim 1, wherein the wash medium is calcium-free.

21. The method according to claim 1, wherein the wash medium further comprises a protein source, at a concentration of between 1 g/l and 30 g/l.

22. The method according to claim 1, wherein the pH of the wash medium is adjusted to a value of 6.8.

23. The method according to claim 1, wherein the incubating is performed by contacting at least $1 \times 10^6$ vital the sperm cells/ml with from $10^{-2}$μg to 100 μg of the episomal vector in a medium, at a temperature of between 17° and 38° C. for a period of time of between 30 minutes and 4 hours.

24. A procedure for the creation of non-human genetically modified individuals, comprising:
bringing a sperm cell, modified in accordance with claim 1 into contact with an egg cell, in order to permit fertilisation thus providing a zygote;
maintaining the zygote under conditions allowing its development into a genetically modified individual.

25. The method according to claim 23, wherein the medium is sterilised and pre-warmed prior to use.

26. The method according to claim 23, wherein the medium is calcium-free.

27. The method according to claim 23, wherein the medium further comprise a protein source, at a concentration of between 1 g/l and 30 g/l.

28. The method according to claim 23, wherein the PH of the medium is adjusted to 6.8.

29. A procedure for the creation of non-human genetically modified individuals, comprising:
bringing a sperm cell, modified in accordance with claim 23, into contact with an egg cell, in order to permit fertilisation thus resulting in a zygote;
maintaining the zygote under conditions allowing development of the zygote into a genetically modified individual.

30. A method for the transfer of nucleotide sequences and/or exogenous genes into animal cells, the method comprising the following steps in sequence:
providing an episomal type vector comprising at least one nucleotide sequence and/or gene sequence of interest which must be transferred into, and expressed in the host;
providing vital male germ cells; and
incubating the vital male germ cells with the episomal vector in a medium having a pH between 6.6 and 6.8 to allow binding of the episomal vector with the cells and optionally entry of the episomal vector into the nucleus of the vital male germ cells.

31. A method for transferring a nucleotide sequence and/or exogenous gene into an animal cell, the method comprising:
- providing an episomal type vector comprising at least one nucleotide sequence and/or gene sequence of interest which must be transferred into, and expressed in the host;
- providing vital male germ cells;
- incubating at least $1 \times 10^6$ of the male germ cells/ml with a suitable amount of the episomal vector in a suitable medium having a pH between 6.6 and 6.8 to allow the binding of the vector with the cells and optionally its entry into the nucleus of the male germ cells, wherein the suitable amount is at least $10^{-2} \mu g$.

32. The method according to claim 31, wherein the suitable amount of the episomal vector is from $10^{-2} \mu g$ to $100 \mu g$.

33. The method according to claim 32, wherein the suitable medium is a composition comprising glucose, at a concentration of between 56 and 69 mM, sodium citrate at a concentration of between 31 and 37 mM, EDTA at a concentration of between 11 and 14 mM, citric acid at a concentration of between 14 and 17 mM and Trizma base at a concentration of between 48 and 59 mM, the final osmolarity typically being between 200 and 320 mOs.

34. The method according to claim 33, wherein the incubating is performed by contacting the male germ cells with the episomal vector in the suitable medium, at a temperature of between 17° and 38° C. for a period of time of between 30 minutes and 4 hours.

\* \* \* \* \*